United States Patent [19]

Aichinger et al.

[11] Patent Number: 5,150,393
[45] Date of Patent: Sep. 22, 1992

[54] X-RAY DIAGNOSTICS INSTALLATION FOR MAMMOGRAPHY

[75] Inventors: Horst Aichinger, Feurth; Sigrid Joite-Barfuss, Erlangen; Karlheinz Koehler, Herzogenaurach, all of Fed. Rep. of Germany

[73] Assignee: Siemens Aktiengesellschaft, Munich, Fed. Rep. of Germany

[21] Appl. No.: 743,443

[22] Filed: Aug. 9, 1991

[30] Foreign Application Priority Data

Sep. 29, 1990 [DE] Fed. Rep. of Germany ....... 4030906

[51] Int. Cl.$^5$ .............................................. A61B 6/04
[52] U.S. Cl. .................................... 378/37; 378/110; 378/112
[58] Field of Search ................. 378/37, 108, 110, 111, 378/116, 96, 19, 112

[56] References Cited

U.S. PATENT DOCUMENTS

| 4,097,741 | 6/1978 | Pfeiler et al. | 250/322 |
| 4,613,982 | 9/1986 | Dornheim et al. | 378/37 |
| 4,763,343 | 8/1988 | Yanaki | 378/110 |
| 4,905,150 | 2/1990 | Aichinger et al. | 364/413.26 |

FOREIGN PATENT DOCUMENTS

| 0063644 | 12/1981 | European Pat. Off. . |
| 3406596 | 9/1985 | Fed. Rep. of Germany . |
| 3641992 | 6/1988 | Fed. Rep. of Germany . |
| 3037527 | 2/1989 | Fed. Rep. of Germany . |
| 8909398 | 11/1989 | Fed. Rep. of Germany . |
| WO8701555 | 3/1987 | PCT Int'l Appl. . |
| 2145221 | 3/1985 | United Kingdom . |

Primary Examiner—Janice A. Howell
Assistant Examiner—Don Wong
Attorney, Agent, or Firm—Hill, Van Santen, Steadman & Simpson

[57] ABSTRACT

An x-ray diagnostics installation for mammography exposures has a radiation detector for making a radiation measurement used to calculate the average parenchyma dose. The radiation detector is disposed on the support table next to the measurement field in which the mammary gland is disposed, and supplies a signal to a computer corresponding to the measured radiation dose at the detector location. The computer is programmed with the dependency of the average parenchyma dose, with respect to the radiation dose at the location of the radiation detector, and thus the computer generates a value corresponding to the average parenchyma dose, obtained by direct measurement rather than by calculation.

1 Claim, 1 Drawing Sheet

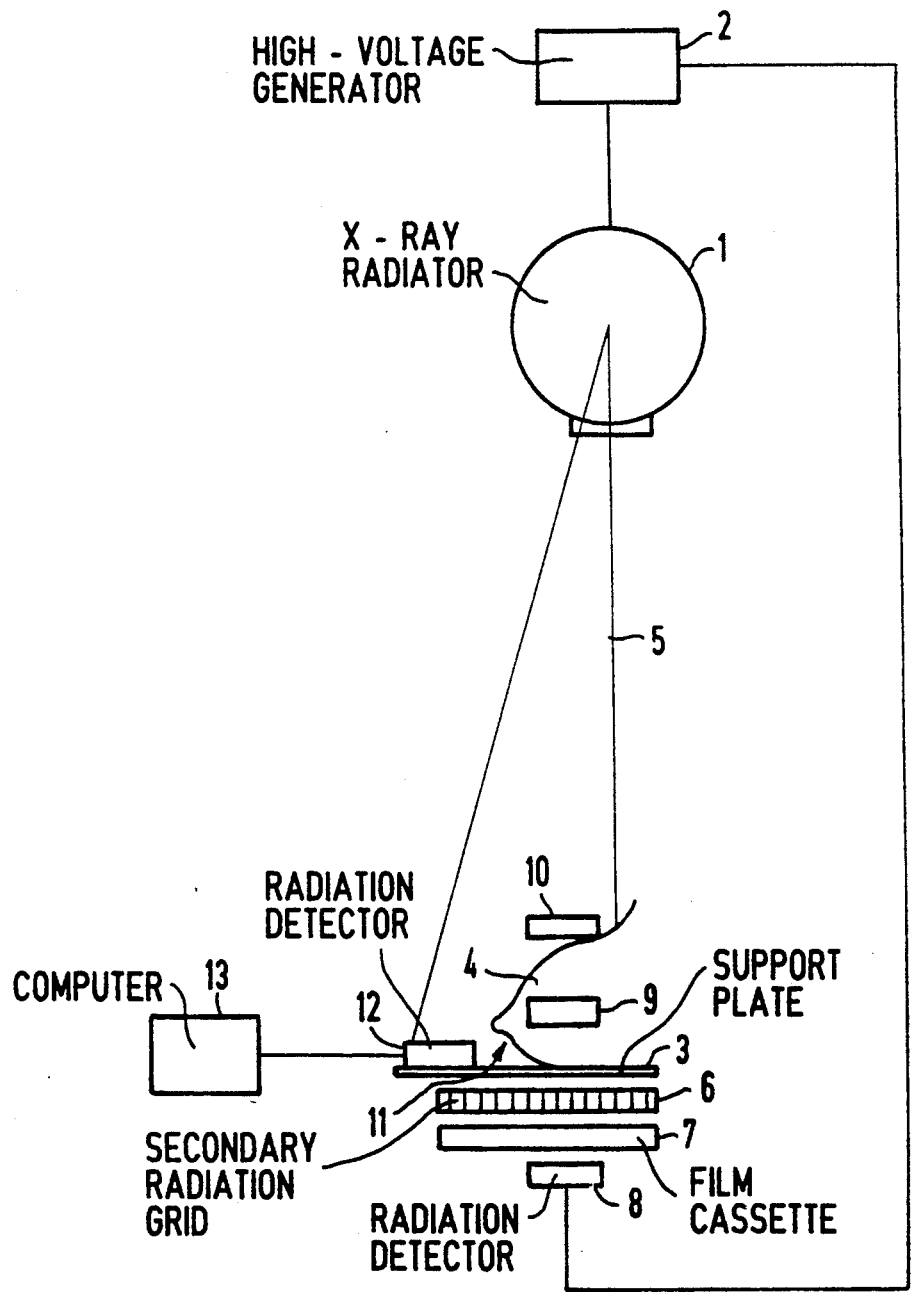

X-RAY DIAGNOSTICS INSTALLATION FOR MAMMOGRAPHY

BACKGROUND OF THE INVENTION

1. Field of the Invention

The present invention is directed to an x-ray diagnostics installation, and in particular to such an installation for mammography exposures.

2. Description of the Prior Art

X-ray installations for making mammography exposures are known which generating include an x-ray radiator, a support plate on which the mammary gland is exposed, and a computer for calculating the average parenchyma dose.

Knowledge of the exposure of the patient to radiation is needed in order to estimate the radiation risk. The dose quantity which is relevant for this purpose is the average parenchyma dose. The average parenchyma dose can be calculated by measuring the entry dose. Such a measurement, however, is usually not possible when preparing x-ray exposures with a patient, because a shadow-producing detector would have to be arranged in front of the exposure subject for this purpose.

For calculating the average parenchyma dose, it is disclosed in European Application 0 325 120 corresponding to U.S. Pat. No. 4,905,150, to employ a computer to which electrical signals are supplied corresponding to various exposure values. The computer calculates the average parenchyma dose from these values according to a given equation. An actual measurement of the average parenchyma dose, consequently, is not undertaken in this known apparatus.

SUMMARY OF THE INVENTION

It is an object of the present invention provide an x-ray diagnostics installation for mammography exposures wherein the average parenchyma dose is calculated using an actual measurement.

The above object is achieved in accordance with the principles of the present invention in an x-ray diagnostics installation having a radiation detector disposed on the support table next to the measurement field. This radiation detector supplies a signal to a computer, which is programmed to generate a value corresponding to the average parenchyma dose based on a known dependency of the average parenchyma dose with respect to the dose measured by the radiation detector. In the x-ray diagnostics installation in accordance with the invention, the dose is measured next to the exposure subject on the support table. The entry dose, and thus the average parenchyma dose corresponding thereto, can be calculated on the basis of the measured dose and on the geometrical position of the radiation detector relative to the exposure subject.

DESCRIPTION OF THE DRAWINGS

The single FIGURE is a schematic block diagram of an x-ray diagnostics installation constructed in accordance with the principles of the present invention.

DESCRIPTION OF THE PREFERRED EMBODIMENTS

As shown in the drawing, an x-ray radiator 1 is fed by a high voltage generator 2 and generates an x-ray beam 5 which transirradiates a mammary gland 4 on a support plate 3. Following the support plate 3 in the radiation propagation direction are a secondary radiation grid 6 for suppressing stray radiation, a film cassette 7 containing x-ray film, and a radiation detector 8 which is a part of an automatic x-ray exposure unit, of a known type. The radiation detector 8 is connected to the high-voltage generator 2, which includes a calculating stage which determines the length of time the x-ray radiator 1 will be energized by the high-voltage generator 2.

The average parenchyma dose is the dose acting in the region 9, indicated by dashed lines, of the mammary 4. This dose could be measured by a radiation detector disposed at a location for making an entry dose measurement, such as at the location 10 indicated by dashed lines. For generating a mammogram, however, a radiation detector placed at the location 10 would be undesirable.

For calculating the average parenchyma dose in accordance with the principles of the present invention, a radiation detector 12, which supplies an electrical signal to a computer 13, is disposed on the support plate 3 next to the measurement field 11 in which the mammary 4 is disposed. The radiation detector 12 measures the dose at its location, and supplies a signal corresponding to this measured dose to the computer 13. The dependency of the incoming signal from the radiation detector 12 on the actual average parenchyma dose is programmed in the computer 13, based on the known geometrical relationship of the position of the radiation detector 12 to the location 9 indicated by dashed lines, so that the computer 13 generates a signal corresponding to the average parenchyma dose.

Although modifications and changes may be suggested by those skilled in the art, it is the intention of the inventors to embody within the patent warranted hereon all changes and modifications as reasonably and properly come within the scope of their contribution to the art.

We claim as our invention:

1. An x-ray diagnostics installation for mammography exposures comprising:

means for generating an x-ray beam emanating from a focus;

a support plate to support an examination subject at a distance from said focus in a measurement field irradiated by said x-ray beam, said examination subject receiving an average parenchyma dose in said measurement field from said means for generating an x-ray beam;

a radiation detector disposed on said support plate next to said measurement field also at said distance from said focus and generating an electrical signal corresponding to radiation from said x-ray beam incident thereon; and computer means connected to said radiation detector programmed with the dependency of said average parenchyma dose with respect to the radiation incident on said radiation detector for generating a value corresponding to said average parenchyma dose.

* * * * *